(12) United States Patent
Larsen et al.

(10) Patent No.: US 7,008,399 B2
(45) Date of Patent: Mar. 7, 2006

(54) ELECTRONICALLY CONTROLLED DEVICE

(75) Inventors: Andre Larsen, Dragor (DK); Thomas Pedersen, Helsingor (DK); Christian Peter Enggaard, Hillerod (DK); Henrik Bendsen, Copenhagen V (DK); Michael Ejstrup Hansen, Veflinge (DK); Claus Schmidt Moller, Fredensborg (DK); Carsten Bitsch Pedersen, Struer (DK)

(73) Assignee: Novo Nordisk A/S, Bagsvaerd (DK)

( * ) Notice: Subject to any disclaimer, the term of this patent is extended or adjusted under 35 U.S.C. 154(b) by 101 days.

(21) Appl. No.: 10/076,025

(22) Filed: Feb. 13, 2002

(65) Prior Publication Data

US 2002/0143288 A1    Oct. 3, 2002

Related U.S. Application Data

(60) Provisional application No. 60/270,107, filed on Feb. 22, 2001.

(51) Int. Cl.
*A61M 31/00* (2006.01)

(52) U.S. Cl. ..................................... 604/65
(58) Field of Classification Search ............ 604/65–67, 604/131, 132, 133, 134, 154, 155, 156, 315; 128/DIG. 12, 13

See application file for complete search history.

(56) References Cited

U.S. PATENT DOCUMENTS

| | | | | |
|---|---|---|---|---|
| 4,838,860 A | * | 6/1989 | Groshong et al. | 604/152 |
| 5,221,268 A | * | 6/1993 | Barton et al. | 604/250 |
| 6,019,745 A | * | 2/2000 | Gray | 604/131 |
| 6,268,722 B1 | * | 7/2001 | Kogure et al. | 324/207.25 |
| 6,547,755 B1 | * | 4/2003 | Lippe et al. | 604/67 |

* cited by examiner

*Primary Examiner*—Manuel Mendez
(74) *Attorney, Agent, or Firm*—Marc A. Began; Reza Green; Richard Bork

(57) ABSTRACT

A device for injecting preparations is controlled by a sealed circuit block (10) containing integrated sensors (17, 21, 22, 23 24) which monitors selected parameters. Two pairs of integrated Hall elements (21, 23 and 22, 24) monitors movements relative to a sine formed magnetic field presented along the perimeter of a multipoled magnetized ring (7). The Hall elements in each pair are displaced 180° magnetically relative to each other and the two pairs of Hall elements are displaced 90° magnetically from each other. Each pair is coupled to a differential amplifier (25, 26) to provide a cosine and a sine signal, respectively. The sine signal is divided by the cosine signal to create a tangent signal as an entrance to a table showing the angle of the movement.

4 Claims, 2 Drawing Sheets

ELECTRONICALLY CONTROLLED DEVICE

Figure 1:
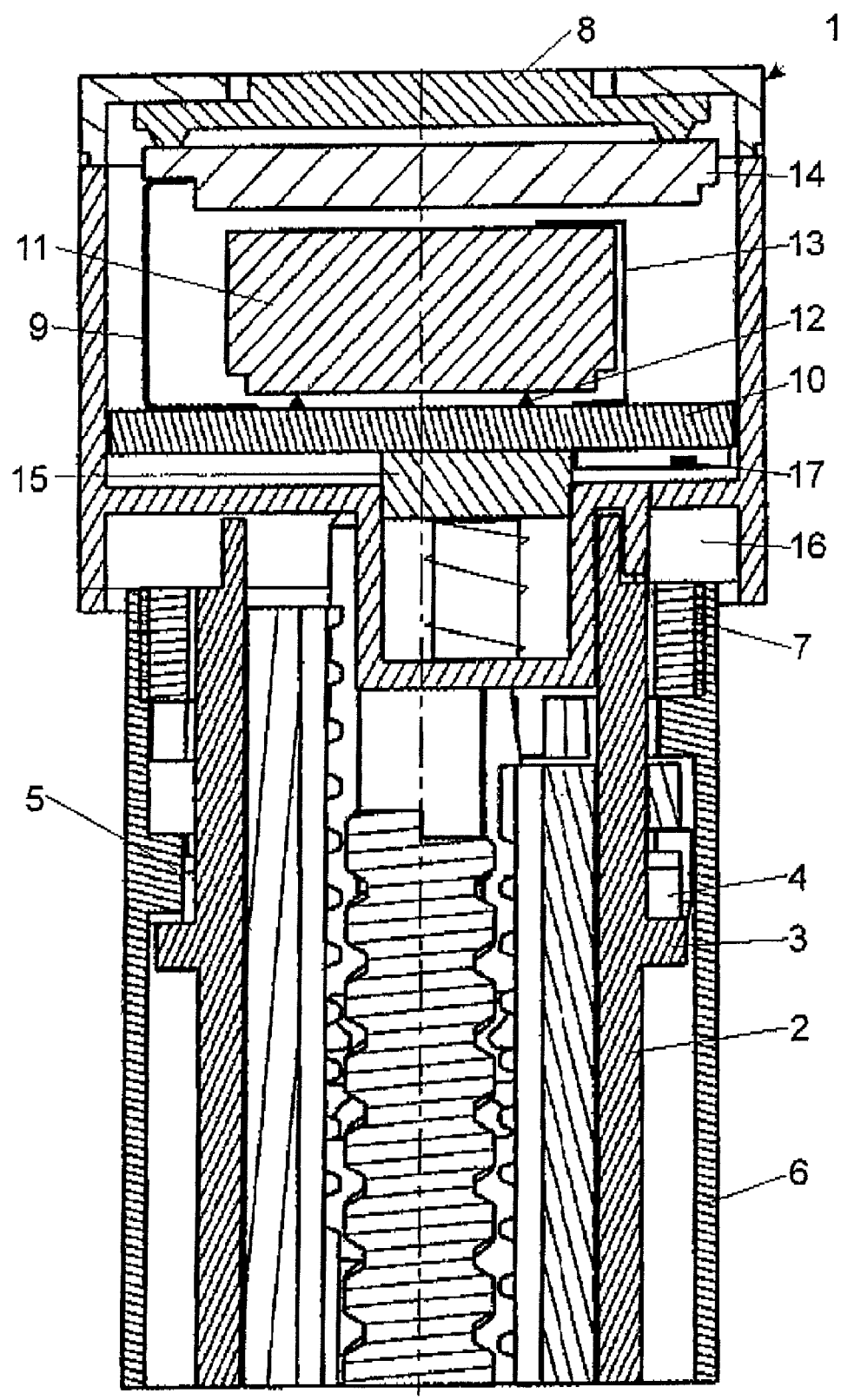

This application claims the benefit of U.S. Provisional Application Ser. No. 60/270,107, filed Feb. 22, 2001.

The invention relates to electrically controlled devices for injecting or infusing medical preparations in the human body.

For patients suffering from diseases, which provoke the need for frequent administration of liquid medicine which is injected or infused into the patient, administration devices has been developed in the form of syringes by which a dose of medicine can easily be set and successively injected by the patient himself. Also pumps have been developed which pumps continuously or semi continuously, i.e. in repetitive small doses, infuse a small flow of the medicine through a catheter into the body of the patient.

To work automatically the pumps have to be equipped with a power supply which can drive the pump. The power supply is mainly an electric battery supplying an electric motor driving a piston into a cartridge to successively press out the content thereof through the catheter. However, pumps may be differently designed as membrane pumps or as another kind of cyclic working pumps, but common to most pumps is, that they are electric powered from an electric battery and controlled by an electric circuit, which is programmed to power the pump in a way ensuring the administration of the correct flow of medicine. The electric circuit can further receive information from sensors distributed in the pump to survey that the pump is working properly and the circuit can control the powering in a way which promotes the correct working.

Originally syringes were mechanically working devices on which the patient could set a wanted dose and thereafter inject the dose by manually pressing down an injection button. In the device described in WO 9730742 the dose setting and the injection is still performed manually but control functions are performed electrically through sensors distributed in the device which sensors sends information to a control circuit by which the device is surveyed.

As described in WO 9733638 the sensors may be switches which occupy "off" or "on" positions reflecting the positions of mechanical parts of the device. Also pulse generators can be realised as switches, which are alternating closed and opened. Signals are sent from the sensors to an electronic circuit in which the signals are evaluated and corresponding messages are sent to a display on which the condition of the device can be read.

The electronic circuit may be a common commercial circuit or an integrated circuit block which is designed and manufactured specifically to be used in the device in question. Once such an integrated circuit block has 1 ft the production line as a functioning circuit it is very reliable, and failing of the device is mainly due to the wiring and connections to sensors outside the circuit. Especially sensors based on mechanical contacts are rather sensible to wear, dust and oxidation.

Consequently it is an objective of the invention to provide an electronic controlled device by which a dose of medicine can be set and injected and in which device wiring and connections outside a sealed integrated electric circuit are reduced to a minimum e. g. to terminals for connection to a power source and an output to a display which commonly will be large relative to the circuit.

This is obtained by an electrically controlled device for injecting or infusing medical preparations into the human body in which devices the controlling is performed by a sealed electric circuit block receiving signals from sensors which monitors selected parameters describing conditions of the device, which device is characterised in that the sensors are integrated in the sealed circuit block and are of a kind with no mechanically opened or closed switches.

The sensors can be light sensors, e. g. photocells, magnetic sensors, e. g. Hall elements, or coils in which a current is induced by an outer magnetic field, load cells which gives of an electric signal when they sense a mechanical pressure. Common to all these sensors are that their electric conditions are changed without involving any wear and dirt sensible switches. Even emission of light can be obtained by the sealed electronic circuit block by establishing of so-called laser wells.

The sealed circuit block, a power supply for this circuit block, and other electronic components connected to said circuit block may be accommodated in one rigid part of the device. Thereby movable electric connections are avoided.

The rigid part of the device may appropriately be a button which can be used for setting or injecting a dose of a medicine.

At least one of the sensors may be a Hall element.

Such a Hall element may be signalled by a movable magnet fixed to a part of the device to monitor the position of this part relative to the part accommodating the electronic circuit block.

The sealed electronic circuit block may comprise a timer which may have a first input for a reset signal, a second input for a signal activating a read out of the timer, and an output to a display displaying the read out of the time lapsed after the latest receipt of a signal on said first input, the injection device further being provided with a sensor connected to the first input of said timer, which sensor gives off a signal when the injection button is pressed to move the piston rod, and with a means for optional sending of a signal to the second input to activate the read out of the electronic circuit.

The electronic circuit in the sealed circuit block may be so designed that a signal sent to said second input opens the energising of the Hall element and other energy consuming sensors. This way the Hall element and other sensors may be energised only when they are going to perform a monitoring function whereas they are switched off when the device is stored. During storage power is still supplied to the timer and memory functions.

The circuit may further be so designed that a signal is sent to said first input when a Hall element in the sealed electronic circuit block detects a change of the position of a magnet relative to the part accommodating the sealed electronic circuit block.

The means optionally sending a signal to the second input may be a switch outside the sealed electronic circuit block. This switch may be a conventional switch in the power supply for the Hall element.

When the device is so designed that the Hall element is not activated during the setting of a dose but is activated during the injection it can count the number of units injected and may at the same time send a signal to said first input.

The magnet may have the shape of a ring having a number of alternating poles along its perimeter To measure the size of an injected dose it is necessary to measure the extent of the rotation of the magnet ring relative to the button accommodating the sealed circuit block. This is obtained by using a number of Hall elements positioned along an arc of a circle which follows a section of said magnet ring. At the start of the rotation the relative position of the magnet ring relative to Hall elements is defined by the magnetic field which is detected by the Hall elements.

On the basis of the field measured a relative angle, the start angle, is calculated. By rotation the field measured varies with the rotation angle and at the end of the rotation the relative angle, the end angle, is calculated. These angles can be found in a table over corresponding detected magnetic fields and angular positions. Such a table can be included in the sealed circuit block. Further it is detected how many times poles having the same polarity are passed and each time this happens the angle between two poles with the same polarity is added to the rotation angle, which is calculated as the end angle minus the start angle. Knowing the number of units which are injected by a 360° rotation the rotation angle can easily be converted to injected units.

In an embodiment of the device according to the invention 4 Hall elements may be used and the magnet ring may have 12 poles. The Hall elements may be so distributed along an arc of a circle that, a first Hall element is positioned facing a north pole a third Hall element is facing a neighbour south pole, a second Hall element is facing the neutral zone between said north pole and said south pole, and a fourth Hall element is facing the neutral zone between said south pole and the succeeding north pole, i. e. the length of the circular arc is 45°.

The magnet poles of the magnet ring creates a sine shaped magnet field with a full sine wave for each pair of poles. With 12 poles on the magnet ring a phase angle of 360° for the sine curve corresponds to 60° of rotation. With the Hall elements placed as described the phase angle at the respective positions of the Hat elements are 0°, 90°, 180°, and 270°, respectively.

The outputs from the first and the third Hal element may be connected to input terminals on a first differential operational amplifier and the outputs from the second and the fourth Hall elements are connected to input terminals on a second differential operational amplifier, and output signals from the differential operational amplifiers are through analogue/digital converters and a normalising circuit lead to a look up table circuit wherein one signal is divided with the other to obtain a tangent function which is used as entrance to a table.

By coupling the Hall elements which are magnetically 180° displaced relative to each other to a differential amplifier immunity against external magnetic fields is obtained. By the 90° displacement between a first set of Hall elements, comprising the first and the third Hall element, and the second set of Hall elements, comprising the second and the fourth Hall element a quadrature measurement is obtained by which one signal is a sine signal and another is a cosine signal. By division of these signals an tangent function is obtained. As tangent value is independent of the amplitudes of the sine and the cosine signals the sensor will be insensitive to variations in the magnetic field strength and consequently independent of the air gap between the magnet ring and the sensor. The tangent value obtained refers to a magnetic angle which can be found in the table. Also account must be taken for the number of times a 360° magnetic cycle has been run through. On the basis hereof the rotation angle for the dose setting drum can be found when the number of poles on the ring is known.

Figure 2:
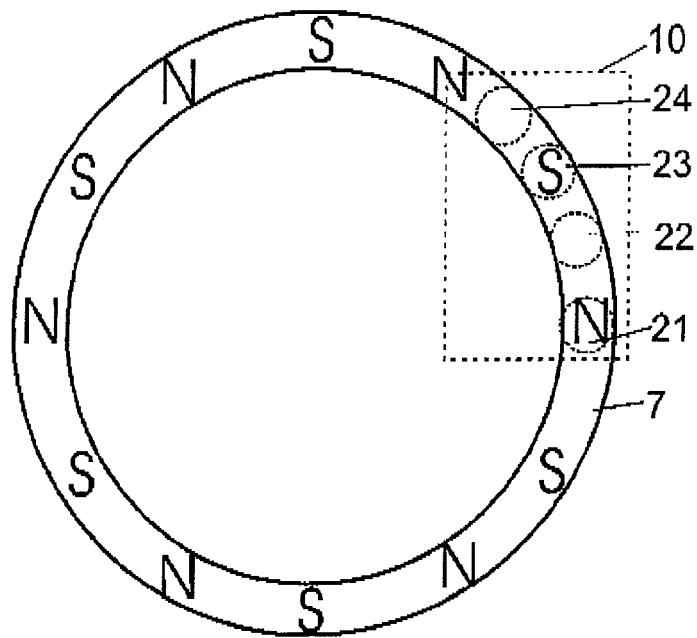

In the following the invention is described in further details with references to the drawing, wherein FIG. 1 shows a detail of an injection device with an integrated circuit block according to the invention FIG. 2 shows schematically the relative positioning of a magnet ring and a sealed circuit block containing four Hall elements.

Figure 3:
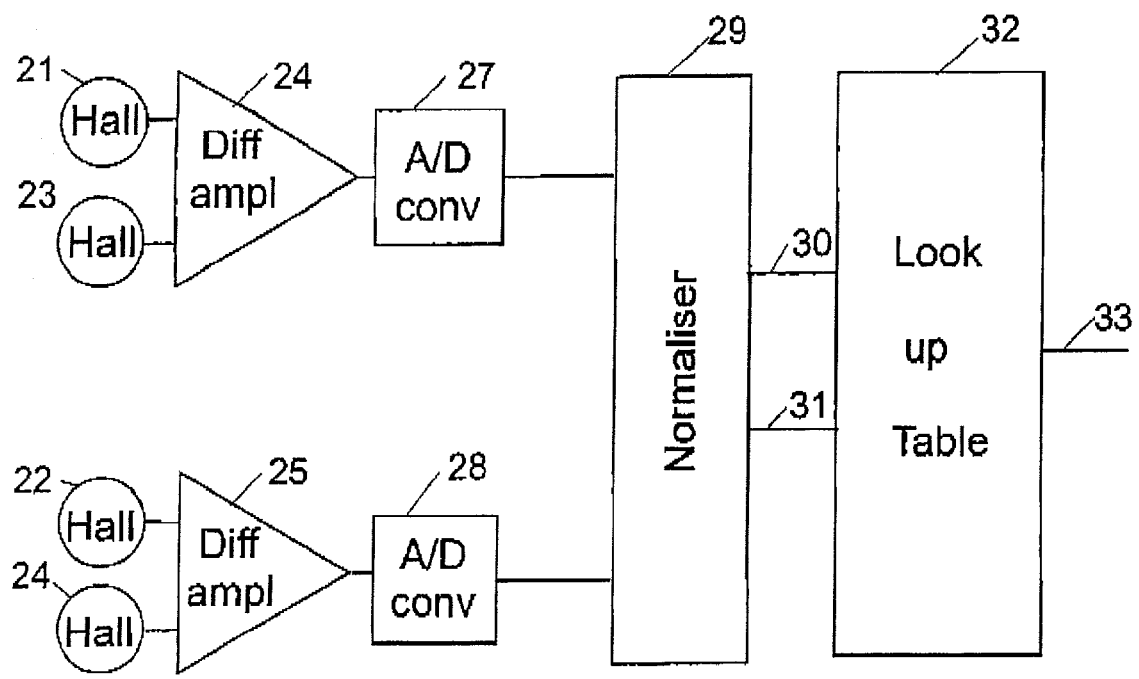

FIG. 3 shows a block diagram of the integrated circuit transforming the readings of the Hall elements into a rotation angle of the dosing mechanism FIG. 1 shows the proximal end of an injection device comprising a combined dose setting and injection button 1, which button is rotated to set a dose and pressed in an axial direction to inject the set dose. The button 1 is fixed to a tubular element 2 so that element 2 will follow as well rotational as axial movements of the button 1.

When the button 1 is rotated to set a dose the tubular element 2 is rotated too. The tubular element 2 has a flange 3 carrying a number of ^-shaped teeth 4 which engages corresponding depressions in an internal circumferential flange 5 in a dose setting drum 6 concentric with the tubular element 2 so that said drum 6 is rotated with said tubular element 2 and the button 1 when said button is rotated to set a dose. When the dose setting drum 6 is rotated it will, due to a not shown thread connection between said drum 6 and a not shown housing concentrically surrounding said dose setting drum 6 and said tubular element 2, be screwed outward in said housing and will lift the button 1 up from the end of said housing.

The button 1 accommodates an electronic unit mounted on a circuit board 15 and comprising a sealed circuit block 10, which is powered by a battery 11 through contacts 12 and 13. From the circuit block 10 output signals are fed through a multi wire cable to a LCD display 14. Further the sealed circuit block 10 has an integrated magnetic sensible component 17 which can give off a signal when it is moved relative to a magnet ring 7 at the upper end of the dose setting drum 6. The magnetic ring 7 is magnetised to have a number of alternating magnetic poles along its perimeter. When the dose-setting drum rotates relative to the button 1 the sensor 17 will give off a signal reflecting the magnetic field sensed by this sensor. The end wall of the button 1 is provided with a window 8 made from a transparent material to allow inspection of the display 14.

The electronic circuit in the sealed circuit block 10 comprises a timer which is started when a dose is injected and the status of which is shown for a while in the display 14 when the button 1 is pressed by pressing the window 8 so that the electronic unit in the button 1 is moved against the force of a spring 19 whereby a button 20 of a switch 18 is pressed to activate said switch.

When the switch 18 is activated it may give off a signal inducing a read out of the stopwatch. When the sensor 17 is a Hall element the switch 18 can be a main switch opening for the energising of this Hall element.

Injection is detected by the sensor 17 when the ring 7 with alternating magnetic poles is rotated relative to the button 1. During the setting of a dose such relative rotation is not performed. At the beginning of its movement the button is moved axially relative to the dose setting drum 6 until the teeth 4 on the flange 3 of the tubular element 2 are moved out of engagement with the depressions in the flange 5 of the dose setting drum 6.

When the button 1 is pressed the activation of the switch 18 will provide a signal which directly or indirectly triggers the circuit block 10 to activate the display 14 for a while to show the status of the timer. As a test all segments are shortly turned on to show that they are all operative before information is shown.

If a dose has been set, further pressing of the button 1 will bring the teeth 4 out of engagement with the depressions in the flange 5 on the dose setting drum 6 whereby said dose setting drum is allowed to rotate relative to the button 1 which relative rotation is detected by the sensor 17 which generates a signal in the integrated circuit block 10 indicating that an injection is made. When the button 1 is released after an injection all the segments are shortly turned on one by one.

The described embodiment allows integration of all electronic components in the button 1 so that only the magnet ring 7 must be provided in the device outside the button, in other embodiments wherein no parts rotate during injection, injection may be detected by using a sensor sensing the movement of a piston rod, which is magnetised with alternating poles. In still other embodiments wherein the button always follows the rotation of the dose-setting drum the rotation to be detected may be the relative rotation between the button and a finger pad at the end of the button, which finger pad follows the button during the dose setting but relative to which the button is rotated during injection. The circuit may be so programmed that such relative movement is only taken as an indication of an injection when the button is pressed.

Although only magnetic acting signal generators are mentioned the use of other, e.g. optical signal generators and sensors lies within the scope of the invention. Also the button in which the electric components are integrated, although it is described as a fixed part of the device, may be removable so that it can be moved from a possible disposable injection device and mounted on a new one, only the devices must be provided with the necessary signaller to generate signals from the sensors. This may appropriately be obtained by moulding such signallers into the syringes by using a mouldable magnetic plastic material.

FIG. 2 schematically shows the magnet ring 7 seen from the end of the device and shows the positions of a first 21, a second 22, a third 23, and a fourth 24 Hall element in the sealed circuit block 10 relative to the poles of the magnet ring 7. This position can be seen as a start position from which the button is screwed away during the setting of a dose and to which the button returns when a set dose has been injected. In the shown embodiment the ring 7 is magnetised to present along it perimeter a sinus shaped magnetic field oscillating 360°, between two poles having the same polarity. With twelve poles along the perimeter of the ring a 360° magnetic angle will correspond to a 60° rotation of the button 1.

When energised during the injection of a set dose the Hall elements 21–24 works together with the magnet ring 7 to monitor the relative rotation of the button 1 relative to the drum 6 as the length of this rotation is proportional with the number of doses injected. In the embodiment shown in FIG. 2 this monitoring is made by leading the output signal from the first 21 and the third 23 Hall elements to the inputs of a differential operational amplifier 25 as shown in FIG. 3. The output signal from the operational amplifier 24, which is an analogue signal proportional with the cosines of the phase angle of the rotation relative to the start position, is digitised by an AD converter 27. It shall be noticed that this phase angle is calculated relative to the magnet poles so that a rotation which brings a Hall element from a pole with one polarity to the next pole with the same polarity is defined as a phase angle of 360° which in the shown example corresponds to a 60° rotation of the drum 6.

Similarly the second 22 and the fourth 24 Hall element is coupled to the inputs of a differential operational amplifier 26 from which the output signal which is proportional with the sinus of phase angle is sent through an analogue digital converter 28. The signals from the AD converters 27 and 28 are normalised in a circuit 29 which has two output terminals 30 and 31 which gives off signals which can address a look up table in a circuit 32 to provide at an output 33 an output signal indicating the rotation angle of the drum 6 relative to the button 1. When the number of units to be injected per 360° rotation of the drum 6 is decided the output from the table can be used for calculating the number of units which have been injected.

The operational amplifiers 25 and 26, the AND converters 27 and 28, the normalising circuit and the look up table can all be integrated in the sealed circuit block. The output signal from the table 32 can also internally in the circuit block 10 be stored in a storage from which a likewise integrated driver for the display 14 is driven to make the display shown the latest injected dose.

Other distributions and numbers of magnetic poles, other numbers and constellations of sensors, and other handling and calculating circuits can be used without deviating from the scope of the invention.

What is claimed is:

1. A device for injecting or infusing medicine wherein: the device comprises a sealed circuit receiving signals from sensors that monitor selected parameters describing conditions of the device, wherein the sensors are integrated in a sealed circuit block and wherein at least one sensor is a Hall sensor and wherein the Hall sensor is signalled by a magnet fixed to a first part of the device to monitor the position of the first part relative to a second part accomdating the sealed circuit block and wherein the sealed circuit block comprises a timer.

2. The device of claim 1, wherein the timer is triggered by movement of the magnet relative to the Hall sensor.

3. The device of claim 1, wherein a first signal is sent to the circuit to energize the Hall sensor and other energy consuming sensors.

4. The device of claim 1, wherein motion of the first part relative to the second part corresponds to a size of a dose of medication and wherein the motion is sensed by the movement of the magnet relative to the Hall sensor and signal(s) from the Hall sensor communicate to the circuit to track the size of the dose and wherein the timer is triggered by injecting or infusing and tracks elapsed time.

* * * * *